United States Patent
Char et al.

(10) Patent No.: US 9,755,025 B2
(45) Date of Patent: Sep. 5, 2017

(54) TRANSPARENT COMPOUND SEMICONDUCTOR AND PRODUCTION METHOD THEREFOR

(71) Applicant: RFTRON CO., LTD., Seoul (KR)

(72) Inventors: Kookrin Char, Seongnam-si (KR); Jisoon Ihm, Seoul (KR)

(73) Assignee: RFTRON CO., LTD., Seoul (KR)

( * ) Notice: Subject to any disclaimer, the term of this patent is extended or adjusted under 35 U.S.C. 154(b) by 279 days.

(21) Appl. No.: 14/390,215

(22) PCT Filed: Apr. 5, 2013

(86) PCT No.: PCT/KR2013/002866
§ 371 (c)(1),
(2) Date: Oct. 2, 2014

(87) PCT Pub. No.: WO2013/151378
PCT Pub. Date: Oct. 10, 2013

(65) Prior Publication Data
US 2015/0048282 A1 Feb. 19, 2015

(30) Foreign Application Priority Data

Apr. 5, 2012 (KR) ........................ 10-2012-0035582
Oct. 4, 2012 (KR) ........................ 10-2012-0109812

(51) Int. Cl.
| | | |
|---|---|---|
| H01B 1/08 | (2006.01) | |
| H01L 31/00 | (2006.01) | |
| H01L 29/24 | (2006.01) | |
| H01L 21/02 | (2006.01) | |
| H01L 31/0224 | (2006.01) | |
| H01L 31/18 | (2006.01) | |
| C23C 14/08 | (2006.01) | |
| C23C 16/40 | (2006.01) | |
| C30B 25/02 | (2006.01) | |
| C30B 29/22 | (2006.01) | |
| H01L 33/42 | (2010.01) | |
| G01N 27/12 | (2006.01) | |

(52) U.S. Cl.
CPC .............. *H01L 29/24* (2013.01); *C23C 14/08* (2013.01); *C23C 16/40* (2013.01); *C30B 25/02* (2013.01); *C30B 29/22* (2013.01); *H01L 21/02414* (2013.01); *H01L 21/02565* (2013.01); *H01L 21/02612* (2013.01); *H01L 31/022466* (2013.01); *H01L 31/1884* (2013.01); *G01N 27/125* (2013.01); *H01L 33/42* (2013.01); *Y02E 10/50* (2013.01)

(58) Field of Classification Search
CPC .............. C23C 14/08; H01L 21/02414; H01L 21/02565; H01L 31/022466; H01L 31/1884; H01L 31/00; C30B 25/02; C30B 29/22; H01B 1/08

USPC ....... 252/500–519.1, 521.1; 257/43; 438/104
See application file for complete search history.

(56) References Cited

U.S. PATENT DOCUMENTS

2012/0225250 A1* 9/2012 Kuznetsov .............. C23C 18/08
428/156

FOREIGN PATENT DOCUMENTS

WO   WO2011027115   *   3/2012   ............... H01B 1/08

OTHER PUBLICATIONS

Hadjarab ("Optical and transport properties of lanthanum-doped stannate BaSnO3" J of Phys D, 40, pp. 5833-5839, pub Sep. 21, 2007).*
Huang ("Electrical properties of BaSn03 in substitution of antimony for tin and lanthanum for barium." JMS, 30, pp. 1556-1560, pub 1995).*
Yasukawa ("High-temperature thermoelectric properties of La-doped BaSnO3 ceramics." Mater Sc Eng B, 173, pp. 29-32, pub 2009).*
Kim ("High Mobility in a Stable Transparent Perovskite Oxide." APE, 5, pp. 061102-1 to 061102-3, pub online May 22, 2012).*
H.F. Wang et al., "Transparent and conductive oxide films with the perovskite structure: La- and Sb-doped BaSnO3", Journal of Applied Physics, May 25, 2007, pp. 106105/1-106105/3, vol. 101, No. 10.
Haifeng Wang et al., "Transparent and conductive oxide films with the perovskite LaxSr1—xSnO3(x<0.15): epitaxial growth and application for transparent heterostructures", Journal of Physics D: Applied Physics, Jan. 8, 2010, pp. 1-8, vol. 43, No. 3.
B Hadjarab et al., "Optical and transport properties of lanthanum-doped stannate BaSnO3", Journal of Physics D: Applied Physics, Sep. 21, 2007, pp. 5833-5839, vol. 40, No. 19.
International Search Report for application No. PCT/KR2013/002866 dated Jul. 22, 2013.
Upadhyay S et al., "Solubility of lanthanum, nickel and chromium in barium stannate", Materials Letters, Jul. 2001, pp. 251-255, vol. 49, No. 5, Elsevier Science B.V.
Upadhyay et al., "Synthesis, structure and electrical behaviour of lanthanum-doped barium stannate", Journal of Physics D: Applied Physics, Apr. 28, 2004, pp. 1483-1491, vol. 37, No. 10, Institute of Physics Publishing, Printed in UK.
Upadhyay et al., "Lanthaum doped barium stannate for humidity sensor", Materials Letters, Aug. 22, 2006, pp. 1912-1915, vol. 61, No. 8-9, Elsevier B.V.
Trari M. et al., "Preparation and characterization of lanthanum doped BaSnO3", Journal of Physics and Chemistry of Solids, Nov. 1, 1994, pp. 1239-1243, vol. 55, No. 11, Pergamon Press, London, GB.
Takahashi R. et al., "Long-range spontaneous structural ordering in barium stannate thin films", Applied Physics Letters, Aug. 25, 2010, pp. 81906-81906, vol. 97, No. 8, American Institute of Physics, Nov. 7, 2016.

(Continued)

*Primary Examiner* — Tri V Nguyen
(74) *Attorney, Agent, or Firm* — Hauptman Ham, LLP

(57) ABSTRACT

The present invention relates to a transparent compound semiconductor and to a production method therefor, and is adapted to provide a transparent compound semiconductor of high stability and charge mobility while being transparent. The transparent compound semiconductor according to the present invention has a composition of $Ba_{1-x}La_xSnO_3$ ($0<x<0.1$) and has a charge mobility of at least 10 $cm^2/V \cdot sec$.

7 Claims, 3 Drawing Sheets

(56) References Cited

OTHER PUBLICATIONS

Luo X. et al., "High carrier mobility in transparent BaLaSnO crystals with a wide band gap", Applied Physics Letters, Apr. 27, 2012, pp. 172112-1-172112-5, vol. 100, No. 17, American Institute of Physics.

European Search Report for corresponding European Patent Application No. 13772003.3 issued on Nov. 3, 2015.

\* cited by examiner (a)

(b)

TRANSPARENT COMPOUND SEMICONDUCTOR AND PRODUCTION METHOD THEREFOR

TECHNICAL FIELD

The present invention relates to a transparent compound semiconductor and a method of fabricating the same, and more specifically, to a transparent compound semiconductor which is transparent and, at the same time, has high stability and high charge mobility, and a method of fabricating the same.

BACKGROUND ART

A trend of the current information technology is to combine functions of electronic devices and functions of display devices. In order to combine the functions of the electronic devices and display devices, the electronic devices need to be transparent.

Therefore, studies on transparent semiconductors and transparent conductors capable of performing functions of the electronic devices while satisfying transparency, and a method of fabricating thereof are being actively conducted. For example, indium tin oxide (ITO) has been developed and used as the transparent conductor, and ZnO has been developed as the transparent semiconductor. However, since those materials have low stability, application thereof as a transparent semiconductor is severely limited.

DISCLOSURE

Technical Problem

Accordingly, the present invention is directed to a transparent compound semiconductor which is transparent and has high stability and high charge mobility, and a method of fabricating the same.

Technical Solution

According to an aspect of the present invention, there is provided a transparent compound semiconductor fabricated by reacting a Ba compound, an La compound, and an Sn compound, and having a composition of $Ba_{1-x}La_xSnO_3$ ($0<x<0.1$) and a charge mobility of at least 10 $cm^2/V \cdot sec$.

In some embodiments, the $Ba_{1-x}La_xSnO_3$ may have the charge mobility of at least 10 $cm^2/V \cdot sec$ at room temperature.

In other embodiments, the $Ba_{1-x}La_xSnO_3$ may be fabricated by mixing the Ba compound, the La compound, and the Sn compound to have the composition of $Ba_{1-x}La_xSnO_3$ ($0<x<0.1$) and reacting the mixed compounds at a temperature of 500° C. to 1500° C.

In still other embodiments, the thickness of the $Ba_{1-x}La_xSnO_3$ may be in the range of 0.4 nm to 400 nm.

In still other embodiments, the $Ba_{1-x}La_xSnO_3$ may have an optical transmittance of at least 90% in the visible light band.

In still other embodiments, the amount of change in resistance of the $Ba_{1-x}La_xSnO_3$ may be less than about 2% when the temperature is elevated and then lowered between the room temperature and 530° C. in an air atmosphere.

In still other embodiments, the $Ba_{1-x}La_xSnO_3$ may be in the form of a single crystal or an epitaxial film.

According to another aspect of the present invention, there is provided a method of fabricating a transparent compound semiconductor including reacting a Ba compound, an La compound, and an Sn compound. The transparent compound semiconductor has a composition of $Ba_{1-x}La_xSnO_3$ ($0<x<0.1$) and a charge mobility of at least 10 $cm^2/V \cdot sec$.

In some embodiments, the $Ba_{1-x}La_xSnO_3$ may have the charge mobility of at least 10 $cm^2/V \cdot sec$ at room temperature. In other embodiments, the Ba compound may be $BaCO_3$ or $BaO$, the La compound may be $La_2O_3$, and the Sn compound may be $SnO_2$.

In still other embodiments, the $Ba_{1-x}La_xSnO_3$ may be fabricated by mixing the Ba compound, the La compound, and the Sn compound to have the composition of $Ba_{1-x}La_xSnO_3$ ($0<x<0.1$) and reacting the mixed compounds at a temperature between 500° C. to 1500° C.

In still other embodiments, the $Ba_{1-x}La_xSnO_3$ may be fabricated by performing a physical or chemical deposition process on a base substrate.

In still other embodiments, the base substrate may include a perovskite metal oxide having an $ABO_3$ structure with a lattice constant of 0.37 to 0.45 nm.

In still other embodiments, the $ABO_3$ may be one of $SrTiO_3$, $LaAlO_3$, $SrZrO_3$, and $BaNbO_3$.

In still other embodiments, the thickness of the $Ba_{1-x}La_xSnO_3$ may be in the range of 0.4 nm to 400 nm.

Advantageous Effects

A transparent compound semiconductor $Ba_{1-x}La_xSnO_3$ ($0<x<0.1$) according to embodiments of the present invention is a transparent compound semiconductor doped with n-type impurities, and has high stability and high charge mobility. That is, the $Ba_{1-x}La_xSnO_3$ is a transparent compound semiconductor having an optical transmittance of at least 90% in the visible light band, stability such that variation in a resistance level is less than 2% when the temperature is elevated and lowered between the room temperature and 530° C. in an air atmosphere, and a charge mobility of at least 10 $cm^2/V \cdot sec$.

In particular, since the $Ba_{1-x}La_xSnO_3$ ($0<x<0.1$) according to the embodiments of the present invention is a transparent compound semiconductor having a high charge mobility of at least 10 $cm^2/V \cdot sec$, it can be applied to a variety of electronic products such as a display device.

MODES FOR CARRYING OUT THE INVENTION

Figure 1:
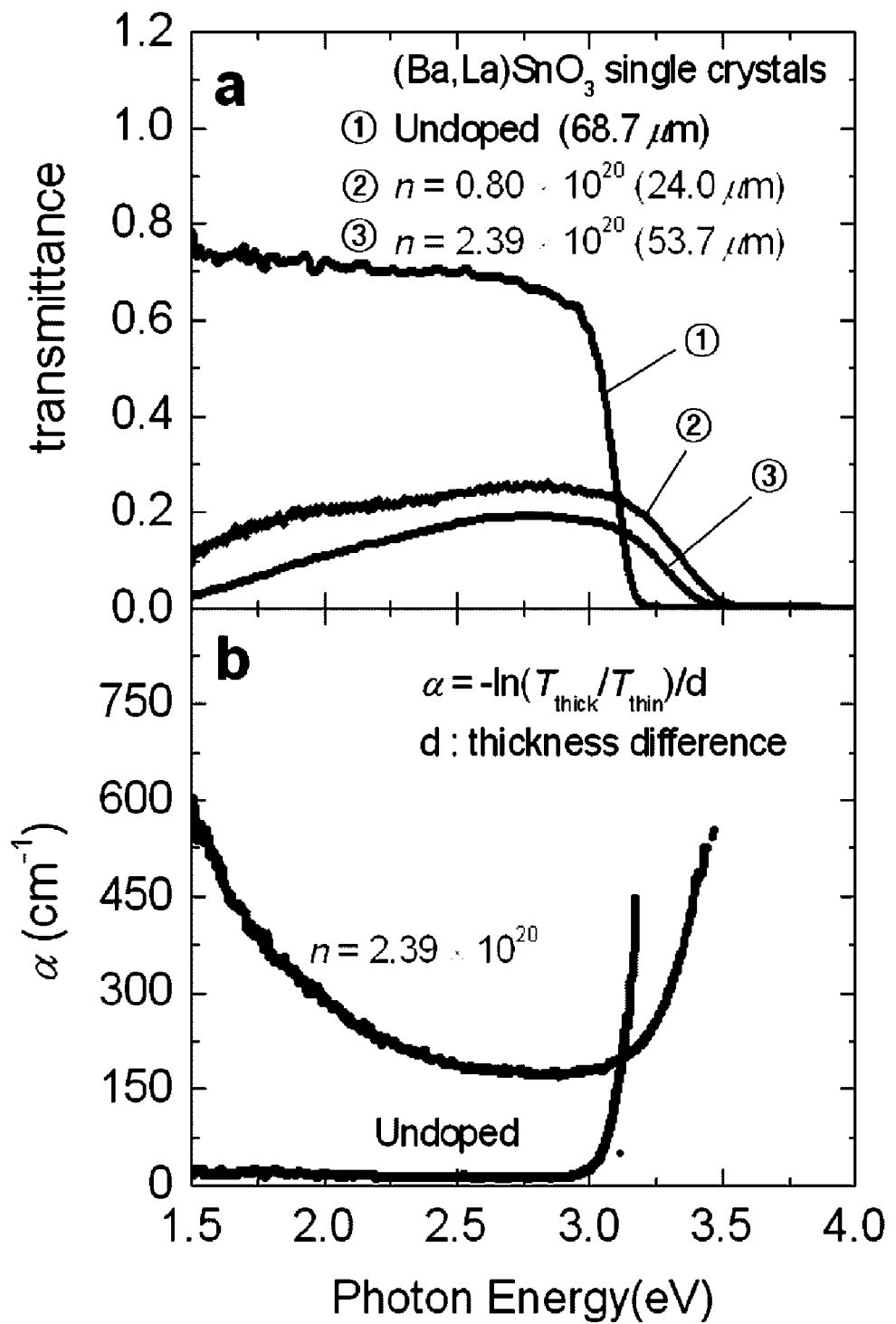
FIG. 1 is a graph showing an optical transmission spectrum of $Ba_{1-x}La_xSnO_3$ ($0<x<0.1$) according to an embodiment of the present invention.

The objects, features, and advantages of the present invention will be more clearly understood from the following detailed descriptions of embodiments taken in conjunction with the accompanying drawings. In the following description, detailed descriptions of related known functions or elements that may unnecessarily make the gist of the present invention obscure will be omitted.

The terms and words used in the specification and claims should not be construed with common or dictionary meanings, but should be construed as meanings and conception coinciding with the spirit of the invention based on a principle that the inventors can appropriately define the concept of the terms to explain the invention in the optimum method. Therefore, embodiments described in the specification and the configurations shown in the drawings are not more than the most preferred embodiments of the present invention and do not fully cover the spirit of the present invention. Accordingly, it should be understood that there may be various equivalents and modifications that can replace those when this application is filed.

Hereinafter, various embodiments will now be described more fully with reference to the accompanying drawings.

A transparent compound semiconductor according to an embodiment of the present invention is an n-type transparent compound semiconductor having a composition of $Ba_{1-x}La_xSnO_3$ ($0<x<0.1$). The $Ba_{1-x}La_xSnO_3$ satisfies a composition ratio of (Ba+La):Sn=1:1.

Here, the composition ratio of $Ba_{1-x}La_xSnO_3$ is $0<x<0.1$ so as to have semiconductor characteristics. Since $BaSnO_3$ is an insulating material (in the case that x=0, that is, La=0), the composition ratio of La needs to be greater than zero. In addition, since $Ba_{0.9}La_{0.1}SnO_3$ is a metal (in the case that La is doped at 0.1), the composition ratio of La needs to be less than 0.1. Accordingly, the $Ba_{1-x}La_xSnO_3$ has a composition ratio of $0<x<0.1$ to have semiconductor characteristics.

The $Ba_{1-x}La_xSnO_3$ may preferably have a thickness of 0.4 nm to 400 nm in order to have good transparency and stability, and to have a charge mobility of at least 10 $cm^2/V \cdot sec$. The $Ba_{1-x}La_xSnO_3$ needs to have such a thickness for the following reasons. First, the thickness of $Ba_{1-x}La_xSnO_3$ may not be less than 0.4 nm since 0.4 nm corresponds to the thickness of a single atomic layer. In addition, when the thickness of $Ba_{1-x}La_xSnO_3$ is greater than 400 nm, transparency may be degraded.

In addition, the $Ba_{1-x}La_xSnO_3$ may be fabricated in the form of a single crystal or an epitaxial film.

$Ba_{1-x}La_xSnO_3$ used as a transparent compound semiconductor according to an embodiment of the present invention may be formed as follows.

First, $Ba_{1-x}La_xSnO_3$ may be formed by doping undoped $BaSnO_3$ with La. $BaSnO_3$ is an insulating material having a lattice constant of 0.41 nm, a bandgap greater than 3 eV, and a transparent property.

Here, the $BaSnO_3$ is used as a base material of $Ba_{1-x}La_xSnO_3$ for the following reasons. First, it is difficult to expect in terms of a basic science that a material formed by doping an insulating material having a bandgap of about 4 eV with a metal material in a concentration of $10^{20}/cm^3$ or less, has a high charge mobility. However, in this embodiment of the present invention, it is discovered that a high charge mobility can be implemented through A-site doping in a perovskite metal oxide having an $ABO_3$ structure, such as $BaSnO_3$. That is, although a perovskite metal oxide has a higher crystallization temperature than other metal compounds having different structures, the perovskite metal oxide has an advantage of providing two cationic sites which can be doped with other material. In particular, $BaSnO_3$, a perovskite metal oxide having a high bandgap of 3 eV may used as the base material of $Ba_{1-x}La_xSnO_3$ in this embodiment of the present invention.

The bandgap of $BaSnO_3$ is greater than 3 eV, which means that $BaSnO_3$ has high transparency. In addition, $Ba_{1-x}La_xSnO_3$ formed using $BaSnO_3$ having such high transparency has several advantages in terms of transparency, compared to silicon with a bandgap of about 1.2 eV or GaAs with a bandgap of about 1.5 eV.

Alternatively, $Ba_{1-x}La_xSnO_3$ may be formed by reacting a Ba compound, an La compound, and an Sn compound. Here, $BaCO_3$ or $BaO$ may be used as the Ba compound, $La_2O_3$ may be used as the La compound, and $SnO_2$ may be used as the Sn compound. For example, the $Ba_{1-x}La_xSnO_3$ may be fabricated by mixing the Ba compound, the La compound, and the Sn compound to have the composition of $Ba_{1-x}La_xSnO_3$ ($0<x<0.1$) and reacting the mixed compounds at a temperature of 500° C. to 1500° C.

Here, the reaction is performed at the temperature of 500° C. to 1500° C. because, when the temperature is lower than 500° C., a crystal structure of $Ba_{1-x}La_xSnO_3$ may not be formed, and when the temperature is higher than 1500° C., the crystal structure of $Ba_{1-x}La_xSnO_3$ may be broken or characteristics as a transparent compound semiconductor may be deteriorated.

The $Ba_{1-x}La_xSnO_3$ may be formed on a base substrate by providing the base substrate using a physical or chemical method while reacting the Ba compound, the La compound, and the Sn compound. As the base substrate, a perovskite metal oxide having an $ABO_3$ structure similar to $BaSnO_3$ having a lattice constant of 0.41 nm may be used. For example, $SrTiO_3$, $LaAlO_3$, $SrZrO_3$, $BaNbO_3$, or the like having a lattice constant of 0.37 nm to 0.45 nm may be used as the base substrate, but the inventive concept is not limited thereto.

In addition, the $Ba_{1-x}La_xSnO_3$ formed by reacting the Ba compound, the La compound, and the Sn compound has a charge mobility of 10 $cm^2/V \cdot sec$ or more. In particular, the $Ba_{1-x}La_xSnO_3$ has a charge mobility of 10 $cm^2/V \cdot sec$ or more at room temperature.

Figure 2:
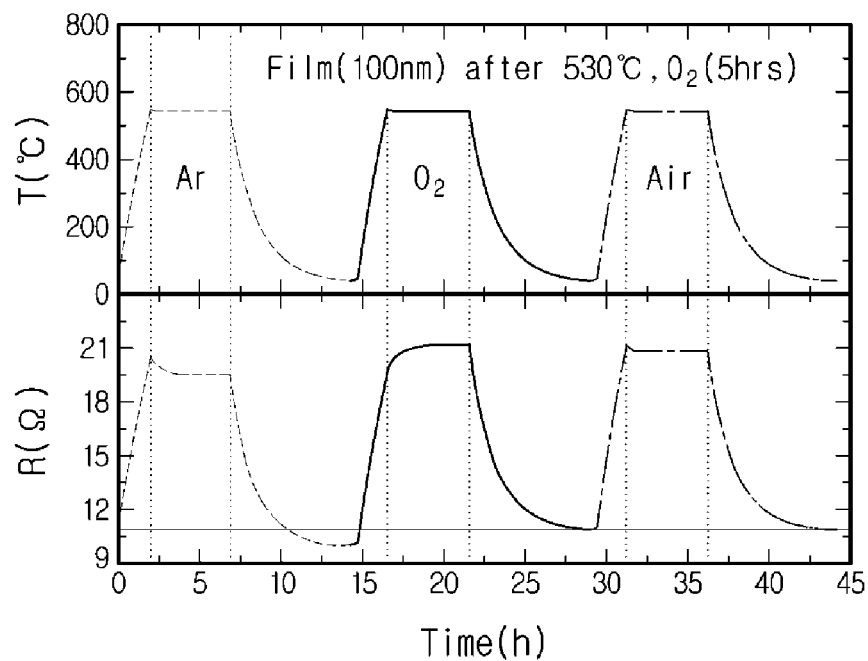
FIG. 2 shows graphs of thermal resistance levels of $Ba_{1-x}La_xSnO_3$ ($0<x<0.1$) according to an embodiment of the present invention.
Figure 2:
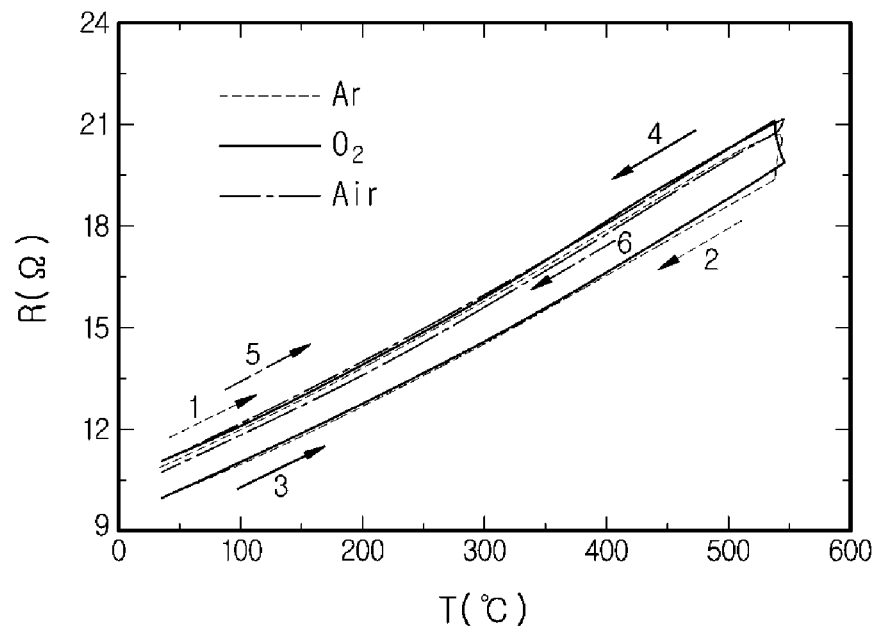
Figure 3:
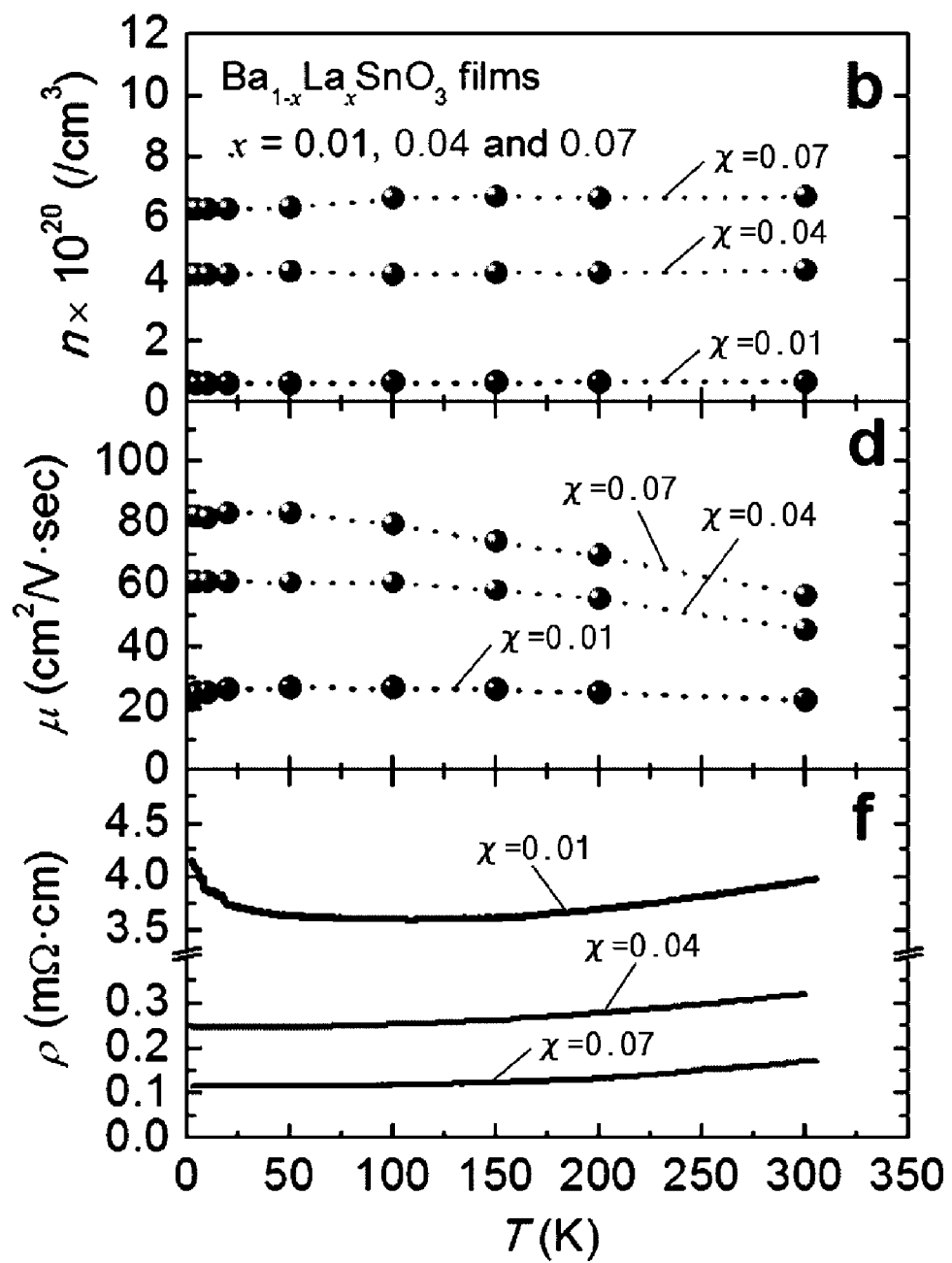
FIG. 3 is a graph showing the charge density, resistance, and charge mobility of $Ba_{1-x}La_xSnO_3$ ($0<x<0.1$) according to an embodiment of the present invention.

Through the graphs of FIGS. 1 to 3, it may be found that the $Ba_{1-x}La_xSnO_3$ according to the embodiment of the present invention has good transparency, stability, and charge mobility.

FIG. 1 is a graph showing an optical transmission spectrum of $Ba_{1-x}La_xSnO_3$ ($0<x<0.1$) according to an embodiment of the present invention.

Referring to FIG. 1, optical transmission spectrums of undoped $BaSnO_3$ and $Ba_{1-x}La_xSnO_3$ according to the embodiment of the present invention are shown. Here, (a) shows a transmittance spectrum of undoped $BaSnO_3$ and transmittance spectrums of doped $BaSnO_3$ ($Ba_{1-x}La_xSnO_3$ according to an embodiment of the present invention), and (b) shows absorption coefficients ($\alpha$) as a function of photon energy of undoped $BaSnO_3$ and doped $BaSnO_3$.

The absorption coefficients ($\alpha$) of the undoped $BaSnO_3$ and the doped $BaSnO_3$ were extracted by measuring transmission coefficients of the same samples with different thicknesses. Optical bandgaps of the undoped $BaSnO_3$ and the doped $BaSnO_3$ (n=$2.39 \times 10^{20}$ $cm^{-3}$) derived from the relationship between $\alpha$ and photon energy were respectively 3.03 eV and 3.01 eV.

That is, it is found that the $Ba_{1-x}La_xSnO_3$ according to the embodiment of the present invention has an optical transmittance of 90% or more in a thin film having a normal thickness.

FIG. 2 shows graphs of thermal resistance levels of $Ba_{1-x}La_xSnO_3$ ($0<x<0.1$) according to an embodiment of the present invention.

Referring to FIG. 2, thermal resistance levels of a $Ba_{0.966}La_{0.04}SnO_{3-\delta}$ thin film according to the embodiment of the present invention were measured in $O_2$, Ar, and air atmospheres. That is, the thermal resistance levels of the $Ba_{0.96}La_{0.04}SnO_{3-\delta}$ thin film were measured after elevating and lowering a temperature between the room temperature and 530° C. in the $O_2$, Ar, and air atmospheres. The $Ba_{0.96}La_{0.04}SnO_{3-\delta}$ thin film may be an epitaxial film.

Here, the graph (a) shows variations in temperature and gas atmosphere, and the graph (b) shows variations in resistance according to the temperature and gas atmosphere. The $Ba_{0.96}La_{0.04}SnO_{3-\delta}$ thin film having a thickness of 100 nm was maintained at a temperature of 530° C. for 5 hours.

(b) shows a relationship between the resistance level and the temperature, and the resistance level was changed by 1.7% in the air atmosphere, lowered by 8% in the Ar atmosphere, and raised by 8% in the $O_2$ atmosphere at the temperature of 530° C. for 5 hours.

In this way, it was found that the $Ba_{1-x}La_xSnO_3$ according to the embodiment of the present invention has high stability such that the variation in resistance level is small even when the temperature is elevated and lowered between the room temperature and 530° C. in the $O_2$, Ar, and air atmospheres. In particular, the $Ba_{1-x}La_xSnO_3$ according to the embodiment of the present invention has high stability such that the variation in resistance level is less than 2% when the temperature is elevated and lowered between the room temperature and 530° C. in the air atmosphere.

FIG. 3 is a graph showing the charge density, resistance, and charge mobility of $Ba_{1-x}La_xSnO_3$ (0<x<0.1) according to an embodiment of the present invention.

Referring to FIG. 3, changes in a charge density n, a resistance ρ, and a charge mobility μ of a $Ba_{1-x}La_xSnO_3$ thin-film according to an embodiment of the present invention, are shown according to a change in the temperature of the $Ba_{1-x}La_xSnO_3$ thin-film. The charge density n, the resistance ρ, and the charge mobility μ are coefficients affected by the temperature. Here, (b, d, and f) respectively represent the charge density n, resistance ρ, and charge mobility μ of the $Ba_{1-x}La_xSnO_3$ thin-film.

It is discovered that the $Ba_{1-x}La_xSnO_3$ according to the embodiment of the present invention has a charge mobility of 10 $cm^2/V \cdot sec$ or more. That is, the $Ba_{1-x}La_xSnO_3$ has a charge mobility of 10 $cm^2/V \cdot sec$ or more at room temperature. Further, when the x value is 0.04 and 0.07, the $Ba_{1-x}La_xSnO_3$ has a charge mobility of 50 $cm^2/V \cdot sec$ or more.

Thus, $Ba_{1-x}La_xSnO_3$ according to the embodiment of the present invention may be transparent and, at the same time, has high stability and high charge mobility. That is, the $Ba_{1-x}La_xSnO_3$ has excellent characteristics of a transparent compound semiconductor. For example, the $Ba_{1-x}La_xSnO_3$ has high transparency such that optical transmittance is 90% or more in the visible light bandwidth, high stability such that variation of the resistance is less than 2% when the temperature is elevated and lowered between the room temperature and 530° C. in the air atmosphere, and high charge mobility of 50 $cm^2/V \cdot sec$ or more (in a doping level of about $10^{20}/cm^3$ at room temperature)

In addition, since the $Ba_{1-x}La_xSnO_3$ according to the embodiment of the present invention has good transparency, stability, and charge mobility, the $Ba_{1-x}La_xSnO_3$ may be used in a variety of industrial fields, such as an electronic industry and a communication equipment industry. In particular, since the $Ba_{1-x}La_xSnO_3$ according to the embodiment of the present invention is an oxide having high stability and a wide bandgap, the $Ba_{1-x}La_xSnO_3$ may be used at a high temperature, less influenced by radiation, and applied to aerospace industry or military industry which consumes large electric energy.

Although a few embodiments have been described, it will be apparent to those skilled in the art that various modifications can be made to the above-described exemplary embodiments of the present invention without departing from the spirit or scope of the invention.

The invention claimed is:

1. A transparent compound semiconductor fabricated by reacting a Ba compound, an La compound, and an Sn compound, the transparent compound semiconductor comprising:
   a composition of $Ba_{1-x}La_xSnO_3$ (0<x<0.1),
   wherein
      a composition ratio of the $Ba_{1-x}La_xSnO_3$ is (Ba+La):Sn=1:1,
      the thickness of the $Ba_{1-x}La_xSnO_3$ is in the range of 0.4 nm to 400 nm, and
      the $Ba_{1-x}La_xSnO_3$ has a charge mobility of at least 10 $cm^2/V \cdot sec$ or more at room temperature.

2. The transparent compound semiconductor of claim 1, wherein, when 0.01≤x≤0.07, the $Ba_{1-x}La_xSnO_3$ has the charge mobility of 10 to 80 $cm^2/V \cdot sec$ at room temperature.

3. The transparent compound semiconductor of claim 1, wherein, when 0.04≤x≤0.07, the $Ba_{1-x}La_xSnO_3$ has the charge mobility of 50 to 80 $cm^2/V \cdot sec$ at room temperature.

4. The transparent compound semiconductor of claim 3, wherein the $Ba_{1-x}La_xSnO_3$ has an optical transmittance of at least 90% in the visible light band.

5. The transparent compound semiconductor of claim 3, wherein the amount of change in resistance of the $Ba_{1-x}La_xSnO_3$ is less than about 2% when the temperature is elevated and lowered between the room temperature and 530° C. in an air atmosphere.

6. The transparent compound semiconductor of claim 1, wherein the $Ba_{1-x}La_xSnO_3$ is in the form of a single crystal or an epitaxial film.

7. A transparent compound semiconductor fabricated by reacting a Ba compound, an La compound, and an Sn compound, the transparent compound semiconductor comprising:
   a composition of $Ba_{1-x}La_xSnO_3$ (0<x<0.1),
   wherein
      a composition ratio of the $Ba_{1-x}La_xSnO_3$ is (Ba+La):Sn=1:1,
      the $Ba_{1-x}La_xSnO_3$ is in the form of a single crystal or an epitaxial film, and
      the $Ba_{1-x}La_xSnO_3$ has a charge mobility of at least 10 $cm^2/V \cdot sec$ or more at room temperature.

* * * * *